United States Patent [19]

van der Meys

[11] Patent Number: Plant 7,478

[45] Date of Patent: Mar. 26, 1991

[54] HYBRID TEA ROSE PLANT NAMED RUIMEYS

[75] Inventor: J. H. van der Meys, EM Maassluis, Netherlands

[73] Assignee: DeRuiter's Nieuwe Rozen B.V., Netherlands

[21] Appl. No.: 392,568

[22] Filed: Aug. 11, 1989

[51] Int. Cl.[5] ..... A01H 5/00

[52] U.S. Cl. ..... Plt./20

[58] Field of Search ..... Plt. 20, 21

[56] References Cited

U.S. PATENT DOCUMENTS

P.P. 5,820 12/1986 DeRuiter ..... Plt. 20

*Primary Examiner*—James R. Feyrer

*Attorney, Agent, or Firm*—Christie, Parker & Hale

[57] ABSTRACT

A new variety of hybrid tea rose having medium red flowers produced on a plant suitable for growing under glass and which produces large quantities of long lasting cut flowers.

2 Drawing Sheets

SUMMARY OF THE INVENTION

The present invention relates to a new and distinct variety of rose plant of the hybrid tea rose class which was discovered by me as a natural mutation in a controlled planting of the rose known as "Ruimeva", U.S. Plant Pat. No. 5,820, the disclosure of which is incorporated herein by reference, and from which is differs in flower coloring. The varietal denomination of the new variety is "Ruimeys".

Among the novel characteristics possessed by this new variety which distinguishes it from its parent and all other varieties of which I am aware are its attractive medium red flowers borne on a plant suitable for production of large quantities of cut flowers. Ruimeys can be reproduced through propagation by cuttings, budding or grafting. Flowers of the new variety are long lasting on the plant and after cutting. Asexual reproduction by budding, grafting, and from cuttings of the new variety as performed in Hazerswoude, Holland, shows that the foregoing and other distinguishing characteristics come true to form and are established and transmitted through succeeding propagation.

The accompanying drawings show typical specimens of the vegatative growth and flowers of the new variety in different stages of development and depicted in color as nearly true as it is reasonably possible to make the same in a color illustration of this character.

BRIEF DESCRIPTION OF THE DRAWING

FIG. 1 is an illustration of cut flowers of the new rose variety of substantially true color; and FIG. 2 is an illustration showing details of the new rose variety but with somewhat darker flower coloring.

DESCRIPTION OF PREFERRED EMBODIMENT

The following is a detailed description of my new variety, with color terminology in accordance with The Royal Horticultural Society Colour Chart (RHSCC) and horticultural terminology in accordance with standard terminology used in UPOV-approved horticultural guidelines. The terminology used in color description herein refers to plate numbers in the aforementioned color chart.

Parentage: Mutation of "Ruimeva".

Class: Hybrid Tea.

As can be seen in the accompanying illustrations, FIG. 1 shows samples of cut flowers of "Ruimeys" depicting the flower form and color.

FIG. 2 shows details of the new variety "Ruimeys". In the illustration there is shown the top of a young shoot, 1; compound three, five and seven leaflet leaves 2, 3, and 4, respectively; a stem, 5; flower buds, 6, after sepals separate and, 7, after petals begin to unfurl; a flower, 8, about one-third to one-half open; and a flower, 9, fully open. Also shown are flower stems 10, 11 and 12, with reproductive organs but without petals.

The following further horticultural observations were made of specimens grown outdoor in Holland.

FLOWER

Blooming habit: Nearly continuous, very floriferous.

A. Bud:

(1) *Size.*—Medium.

(2) *Form.*—Pointed, ovate.

(3) *Color.*—As sepals divide, bud color is near 45A with yellow infusion toward base.

(4) *Sepals.*—Longer than bud, simple to extremely foliated.

(5) Penduncle.—Length — about 10 or more cm. Aspect — straight. Strength — erect. Color — medium green.

B. Bloom:

Flower:

*Average size.*—Medium to large; viewed from top — irregularly rounded; viewed from side: (A) upper part of fully opened flower — flattened convex; (B) lower part of fully opened flower — flattened convex.

(1) *Size.*—Average size when fully expanded — about 12 to 14 cm.

(2) *Borne.*—Singly, one to a stem.

(3) *Form.*—Ovoid at first, becoming high centered then convex at maturity, outer petals reflex to points, inner petals reflex and/or roll under.

(4) *Petalage.*—Number of petals under normal conditions — about 20, semi-double.

(5) *Color.*—After sepals fall and petals unfurl, predominant flower color is medium red 45A, B, C to 43A. Coloring is similar on petals top and reverse sides. Color is substantially stable. On reverse, petals may be imbued with light white underlay toward point of petal attachment approaching, near 155B. Overall tonality from a distance is an attractive medium rod.

(6) *Flowering.*—Medium number of flowers.

(7) *Flower pedicel.*—Few hairs or prickles.

Petals:

(1) *Texture.*—Firm, thick.

(2) *Appearance.*—Inside velvety and outside satiny.

(3) *Form and size.*—Broad obovate, large, slight undulation at margin.

(4) *Arrangement.*—Regularly arranged, imbricated.

(5) *Petaloids in center.*—Few.

(6) *Persistence.*—Drop off cleanly.

(7) *Fragrance.*—Slight.

(8) Lasting quality.—Long lasting quality on plant and as cut flower.

REPRODUCTIVE ORGANS

A. Stamens, filaments and anthers:

*Arrangement and color.*—Regularly arranged around styles; color — filaments red.

B. Pollen:

*Color.*—Yellow orange.

C. Styles: Even, long, red, bunched, significant hairiness in upper half.

D. Stigma: Full, above anthers.

E. Hips: Medium to large, pitcher-shaped.

PLANT

A. Form: Upright.

B. Growth: Vigorous.

C. Foliage: Compound 3, 5 and 7 leaflets.

(1) *Size.*—Medium.

(2) *Quantity.*—Abundant.

(3) *Color.*—Foliage at time of first flowering — medium green.

(4) *Shape.*—Oval, pointed.

(5) *Texture.*—Upper side is glossy; under side is matte.

(6) *Edge.*—Serrate.

(7) *Serration.*—Ordinary, acuminate apices.

(8) *Leaf stem.*—Color — medium green.

(9) *Stipules.*—Medium length, slightly bearded, light green, distinct auricle.

(10) *Leaflet.*—Cross section — slight convex; terminal leaflet — length of blade, medium; maximum width, narrow; shape of base, rounded Petiole length — medium.

D. Wood:

(1) *New wood.*—Color — purple.

(2) *Old wood.*—Color — medium green.

E. Prickles (thorns):

(1) *Prickles.*—Present, quantity (main stalk) ordinary; on laterals from stalk — ordinary; form — straight and some slanted slightly downward shape of upper side — flat; shape of lower side — concave; number of short prickles ($\leqq 5$ mm) — medium; number of long prickles ($>5$ mm — medium to many; color — tan to light pale pink; position — irregular; on pedicel — very few.

F. Winter hardiness: Needs protection outdoors in severe climates.

I claim:

1. A new and distinct variety of rose plate of the hybrid tea rose class, substantially as shown and described, characterized particularly by a plant suitable for growing under glass and which produces large quantities of long lasting, medium red cut flowers.

* * * * *

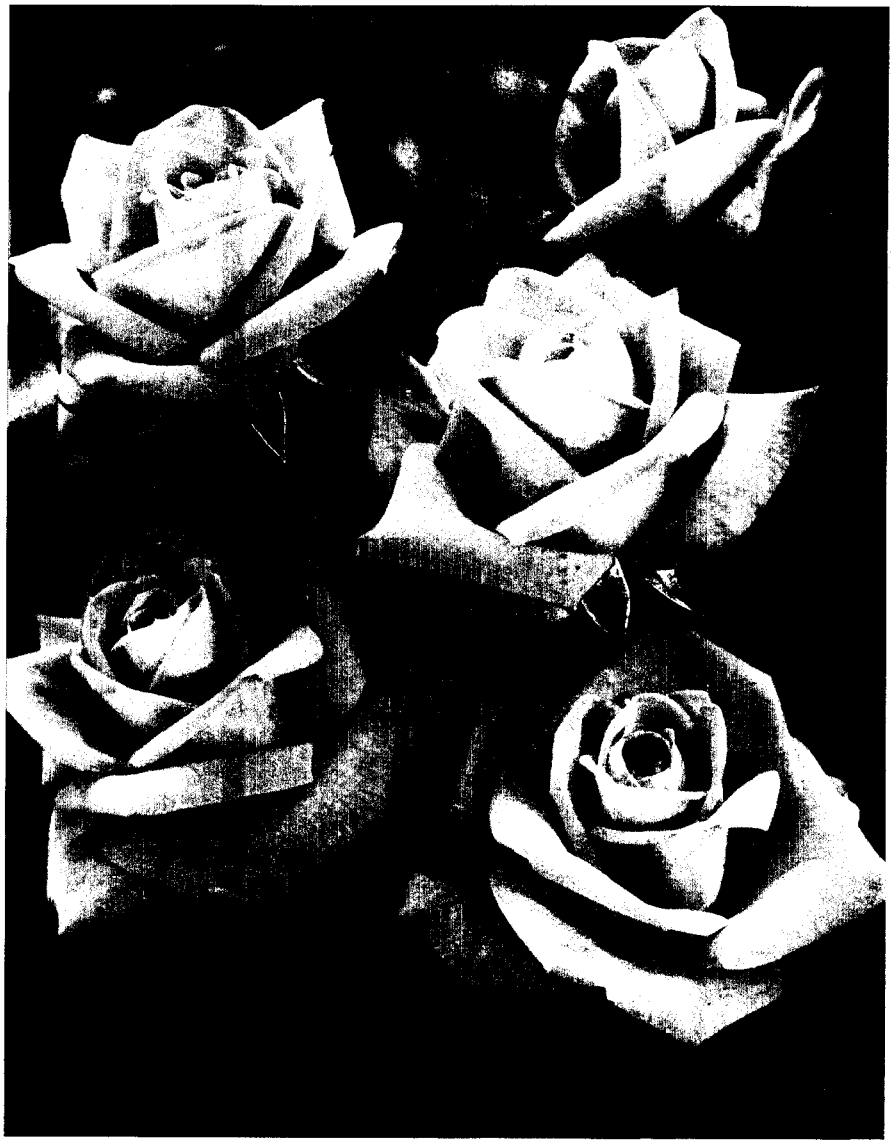

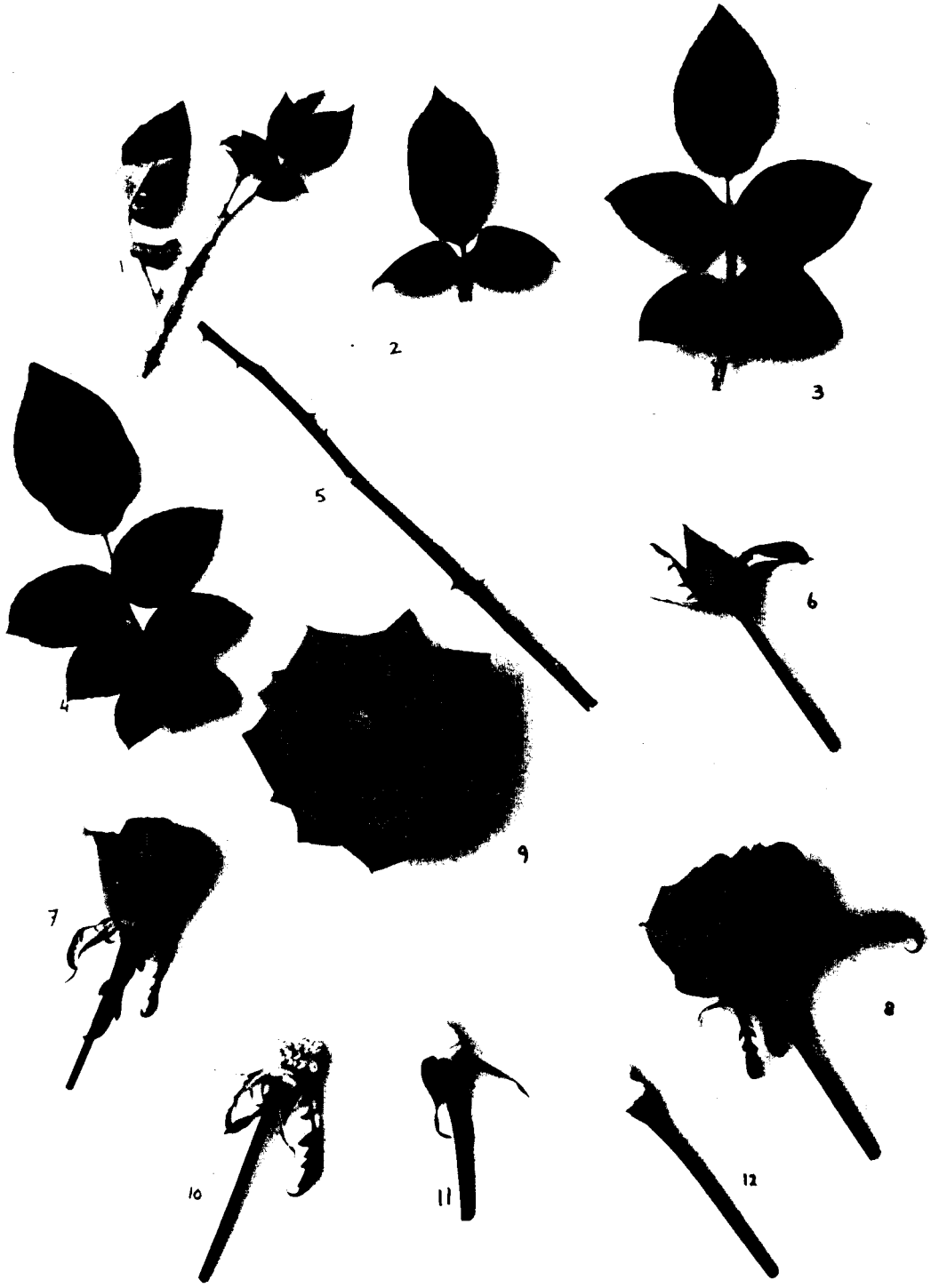
1
2
3
4
5
6
7
8
9
10
11
12

UNITED STATES PATENT AND TRADEMARK OFFICE

CERTIFICATE OF CORRECTION

PATENT NO. : Plant 7,478

DATED : March 26, 1991

INVENTOR(S) : J.H. van der Meys

It is certified that error appears in the above-identified patent and that said Letters Patent is hereby corrected as shown below:

Column 1, line 8, after"which" change "is" to -- it --.
Column 1, line 25, change "vegatative" to -- vegetative --.
Column 2, line 18, before "FLOWER" insert -- 1. --.
Column 3, line 6, after "medium" change "rod" to -- red --.
Column 3, line 9, before "Petals:" insert -- C. --.
Column 3, line 21, before "REPRODUCTIVE ORGANS" insert -- 2 --.
Column 3, line 33, before "PLANT" insert -- 3. --.
Column 4, line 25, change "(> 5 mm" to -- (> 5 mm) --.

Column 4, line 32, after "rose" change "plate" to -- plant --.

Signed and Sealed this

Tenth Day of November, 1992

*Attest:*

DOUGLAS B. COMER

*Attesting Officer*

*Acting Commissioner of Patents and Trademarks*